(12) United States Patent
Ohno et al.

(10) Patent No.: US 6,462,223 B2
(45) Date of Patent: Oct. 8, 2002

(54) ESTER AND PROCESS FOR PRODUCING THE SAME

(75) Inventors: Mitsuru Ohno, Tsukuba; Noritsugu Yamasaki, Himeji; Satoru Nose, Tsukuba, all of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/845,207

(22) Filed: May 1, 2001

(65) Prior Publication Data

US 2001/0020103 A1 Sep. 6, 2001

Related U.S. Application Data

(62) Division of application No. 09/704,576, filed on Nov. 3, 2000, now Pat. No. 6,297,388.

(30) Foreign Application Priority Data

Nov. 5, 1999 (JP) .......................................... 11-315291

(51) Int. Cl.$^7$ .............................................. C07C 67/03
(52) U.S. Cl. ........................................ 560/96; 560/190
(58) Field of Search ................................ 549/263, 292, 549/274; 560/96, 90

(56) References Cited

U.S. PATENT DOCUMENTS 4,612,379 A * 9/1986 Kaneko et al. ............. 549/274
5,256,800 A * 10/1993 Kaneko et al. ............. 549/274

FOREIGN PATENT DOCUMENTS

| CH | 659060 A5 | 12/1986 |
|---|---|---|
| EP | 0819680 A | 1/1998 |
| JP | 5978146 | 5/1984 |
| JP | 324461 | 4/1991 |

OTHER PUBLICATIONS

Sato et al., Tetrahedron, 47 (30), 5689, 1991.*
Bodurow et al., Org. Prep. Proced. Int. (1990), 22(1), 109–11 CAS Abstract.*
Jun–ichi Sakai et al., "Baker's Yeast Mediated Bioreduction of Prochiral Ketones Having 6–(4–Oxo–1, 3–dioxinyl) Group 1)", Chemistry Letters, 1990, pp. 901–904.
David M. Birney et al., "Chemoselectivity in the Reactions of Acetylketene and Acetimidoylketene: Confirmation of Theoretical Predictions" 1997, pp. 7114–7120.
Masanobu Hidai, "Introduction to Homogeneous Catalyst and Heterogeneous Catalyst", Dec. 20, 1983, Chemistry Seminar 11, pp. 48–49.
J. Kiji et al., "Bull. Chem. Soc. Jpn.", vol. 69, No. 4, 1996, pp. 1029–1032.
N. Haddad et al., "J. Org. Chem.", vol. 62, No. 22, 1997, pp. 7629–7636.
M. A. Titus et al., "J. Am. Chem. Soc.", vol. 113, No. 15, 1991, pp. 5775–5783.
M. Sato et al., "Chem. Pharm. Bull.", vol. 38, No. 1, 1990, pp. 94–98.
A.K. Beck et al., "Chimia", vol. 45, No. 12, 1991, pp. 379–382.
E.–I. Negichi et al., "Tetrahedron Letters", vol. 29, No. 51, 1988, pp. 6745–6748.
Y. Noda, "D. Seebach: Helv. Chim. Acta", vol. 70, No. 8, 1987, pp. 2137–2145.
T. Kondo et al., "J. Organomet. Chem.", vol. 473, No. 1–2, 1994, pp. 163–173.
S.–I Murahashi et al., "J. Org. Chem.", vol. 58, No. 6, 1993, pp. 1538–1545.
R. Takeuchi et al., "J. Org. Chem.", vol. 54, No. 8, 1989, pp. 1831–1836.
B. A. Patel et al., "J. Org. Chem.", vol. 44, No. 6, 1979, pp. 918–921.
T. Okano, N. Okabe, "Bull. Chem. Soc. Jpn.", vol. 65, No. 10, 1992, pp. 2589–2593.
T. Kondo et al., "Tetrahedron Lett.", vol. 29, No. 31, 1988, pp. 3833–3836.
M. Sato et al., "Heterocycles", vol. 26, No. 10, 1987, pp. 2611–2614.

* cited by examiner

Primary Examiner—Joseph K. McKane
Assistant Examiner—Kamal Saeed
(74) Attorney, Agent, or Firm—Birch, Stewart, Kolasch & Birch, LLP

(57) ABSTRACT

6-Alkoxycarbonylmethyl-4H-1,3-dioxin-4-one derivatives are produced by reacting a 6-halomethyl-4H-1,3-dioxin-4-one derivative with carbon monoxide and an alcohol or water, and 3-oxopentanedicarboxylic acid esters are further produced by reacting the above derivatives with an alcohol or water. Such a process can produce 3-oxopentanedicarboxylic acid esters in an easy and simple and efficient manner.

3 Claims, No Drawings

ESTER AND PROCESS FOR PRODUCING THE SAME

This application is a divisional of application Ser. No. 09/704,576, filed on Nov. 3, 2000, now U.S. Pat. No. 6,297,388 the entire contents of which are hereby incorporated by reference and for which priority is claimed under 35 U.S.C. § 120; and this application claims priority of application Ser. No. 315291/1999 filed in Japan on Nov. 5, 1999 under 35 U.S.C. § 119.

FIELD OF THE INVENTION

The present invention relates to 6-alkoxycarbonylmethyl-4H-1,3-dioxin-4-one derivatives, a process for producing the same, intermediates which are important in the process, and a process for producing 3-oxopentanedicarboxylic acid esters using the above derivatives.

BACKGROUND OF THE INVENTION

3-Oxopentanedicarboxylic acid esters are compounds useful as intermediates of fine chemicals, such as medicinals and agrochemicals, and as raw materials for polyesters.

Organic Syntheses, Collective Volume 1, page 10 and page 237, for instance, discloses a technique of producing 3-oxopentanedicarboxylic acid which comprises treating citric acid with fuming sulfuric acid to give acetonedicarboxylic acid and esterifying this dicarboxylic acid. In this process, however, the intermediate acetonedicarboxylic acid is unstable and readily undergoes decomposition by heat or by an acid or alkali, for instance. Therefore, when this process is conducted on an industrial scale, the yield of and the selectivity for the desired product 3-oxopentanedicarboxylic acid ester are low.

In Japanese Patent Publication No. 24461/1991 (JP-3-24461B) and Japanese Patent Application Laid-Open No. 78146/1983 (JP-59-78146A), there is reported a method of synthesizing 3-oxopentanedicarboxylic acid from diketene, an alkyl nitrite and carbon monoxide using a palladium catalyst. For obtaining the alkyl nitrite, however, it is in general necessary to react a nitrogen oxide, such as nitrogen monoxide, nitrogen dioxide, dinitrogen trioxide or dinitrogen tetraoxide, which requires care in handling, with an alcohol or water. This reduced the workability and reaction operability.

Therefore, these processes cannot be said to be advantageous from the industrial practicability viewpoint. Further, these processes are essentially incapable of synthesizing unsymmetrical diesters (namely diesters having a structure such that the two ester groups have different alkoxy moieties) and, even if they could be synthesized, they would be obtained only in the form of a mixture of unsymmetrical and symmetrical diesters.

In Swiss Patent No. 659060, a method is disclosed which uses an acetoacetate ester and a chloroformate ester as starting materials. However, this method uses liquid ammonia and sodium amide, which are not always easy to handle on an industrial scale, and, therefore, cannot be said to be an advantageous method from the industrial production viewpoint, either.

On the other hand, Chemistry Letters, 1990, volume 6, pages 901–904 and the Journal of Organic Chemistry, vol. 62, No. 21, page 7114 (1997), for instance, describe a ring-opening reaction of a 6-substituted-4H-1,3-dioxin-4-one under the action of an alcohol or water.

Further, in M. Hidai and M. Ichikawa: "Kagaku Seminar, 11, Kin'itsu Shokubai to Fukin'itsu Shokubai Nyumon—Korekarano Shokubai Kagaku (Seminar in Chemistry, 11, Homogeneous and Heterogeneous Catalysts, An Introduction—Catalytic Chemistry in the Future)", published by Maruzen Co. (1983), page 49, for instance, there is described an ester synthesis by the carbonylation reaction of an aryl halide using a palladium catalyst.

However, there is no description of 6-alkoxycarbonylmethyl-4H-1,3-dioxin-4-ones and there is no example known of the application of these reaction systems to 6-alkoxycarbonylmethyl-4H-1,3-dioxin-4-ones.

SUMMARY OF THE INVENTION

Accordingly, it is an object of the present invention to provide a process by which 3-oxopentanedicarboxylic acid esters can be produced in an industrially advantageous manner (e.g. safely and at low cost), and intermediates for use in that process.

Another object of the invention is to provide a process by which unsymmetrical 3-oxopentanedicarboxylic acid esters can be produced with good efficiency, and intermediates for use in that process.

A further object of the invention is to provide a process by which 3-oxopentanedicarboxylic acid esters can be produced with good efficiency, and intermediates for use in that process.

As a result of intensive investigations made to solve the above problems, the present inventors found that specific cyclic esters can be synthesized efficiently by reacting a specific halogen compound with carbon monoxide and an alcohol or water and, further, that 3-oxopentanedicarboxylic acid esters can be produced from these cyclic esters in an industrially advantageous manner. These findings have now led to completion of the present invention.

Thus, the cyclic esters of the present invention are represented by the following formula (1):

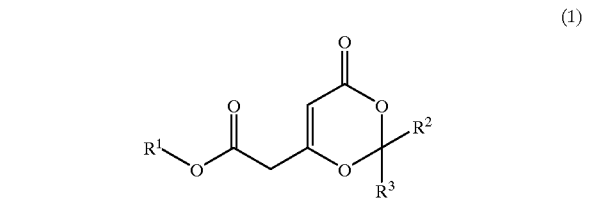

wherein $R^1$, $R^2$ and $R^3$ are the same or different and each represents a hydrogen atom or a chain or cyclic aliphatic hydrocarbon group, which may optionally be further substituted.

In the above formula (1), $R^1$ may be a straight or branched $C_{1-6}$ alkyl group, a $C_{3-10}$ cycloalkyl group or a $C_{6-10}$ aryl-$C_{1-4}$ alkyl group and $R^2$ and $R^3$ are the same or different and each may be a hydrogen atom or a $C_{1-4}$ alkyl group.

The present invention also includes a process for producing the above cyclic esters which comprises the step of reacting a halogen compound represented by the formula (2) with carbon monoxide and an alcohol or water represented by the formula (3), as shown below:

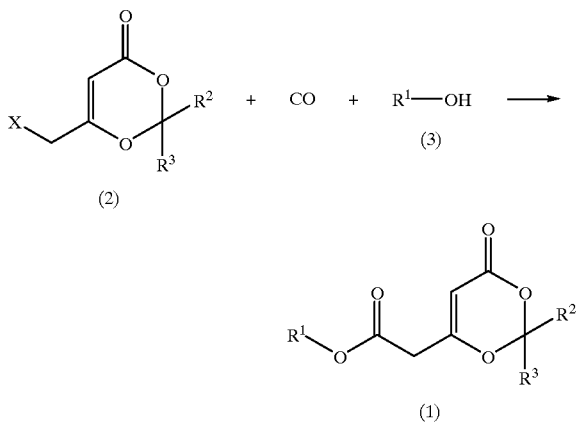

(2) + CO + R¹—OH ⟶ (3)

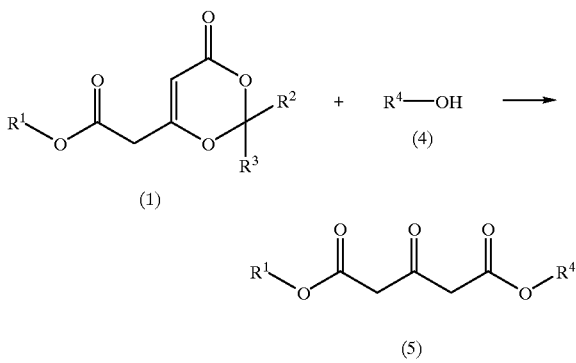

(1)

wherein, X represents a halogen atom and $R^1$, $R^2$ and $R^3$ are as above defined in the formula (1).

In this process, the reaction may be carried out in the presence of a catalyst comprising a platinum group metal (e.g. palladium) (a platinum group metal as a simple substance or a platinum group metal-containing compound).

The present invention further includes a process for producing dicarboxylic acid esters represented by the formula (5) which comprises the step of reacting the above cyclic esters with an alcohol or water represented by the formula (4), as shown below:

(1) + R⁴—OH (4) ⟶ (5)

wherein, $R^4$ represents a hydrogen atom or a chain or cyclic aliphatic hydrocarbon group, which may optionally be substituted, and $R^1$ to $R^3$ are as above defined.

The present invention further includes halogen compounds represented by the formula (2) given below (in particular compounds in which X is a bromine or iodine atom). These compounds are useful as intermediates for the production of the above cyclic esters.

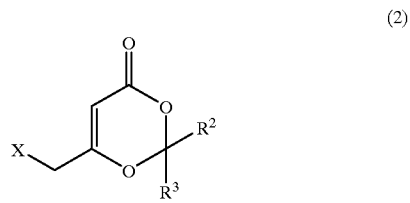

(2)

In the formula, X is a halogen atom and $R^2$ and $R^3$ are as above defined in the formula (1).

DETAILED DESCRIPTION OF THE INVENTION

[Cyclic Esters]

Referring to the cyclic esters (6-alkoxycarbonylmethyl-4H-1,3-dioxin-4-one derivatives) represented by the above formula (1), the aliphatic chain hydrocarbon group represented by $R^1$, $R^2$ and/or $R^3$ includes straight chain or branched chain hydrocarbon groups, for example alkyl, alkenyl, alkynyl groups. The aliphatic cyclic hydrocarbon group (alicyclic hydrocarbon group) includes saturated or unsaturated aliphatic cyclic groups, for example cycloalkyl, cycloalkenyl, cycloalkynyl groups.

Among the alkyl groups, there may be mentioned, for example, straight or branched $C_{1-10}$ alkyl groups (preferably $C_{1-6}$ alkyl groups, in particular $C_{1-4}$ alkyl groups), such as methyl, ethyl, propyl, isopropyl, butyl, isobutyl and tert-butyl groups.

Among the alkenyl groups, there may be mentioned, for example, straight or branched $C_{2-6}$ alkenyl groups (in particular $C_{2-4}$ alkenyl groups), such as vinyl, allyl, isopropenyl, 1-butenyl and 2-butenyl groups.

Among the alkynyl groups, there may be mentioned, for example, straight or branched $C_{2-6}$ alkynyl groups (in particular $C_{2-4}$ alkynyl groups), such as ethynyl, propynyl, 1-butynyl and 2-butynyl groups.

Among the cycloalkyl groups, there may be mentioned, for example, $C_{3-10}$ cycloalkyl groups, preferably $C_{4-8}$ cycloalkyl groups (in particular $C_{4-6}$ cycloalkyl groups), such as cyclopropyl, cyclobutyl, cyclopentyl, cyclohexyl and cyclooctyl groups.

Among the cycloalkenyl groups, there may be mentioned, for example, $C_{3-10}$ cycloalkenyl groups, preferably $C_{4-8}$ cycloalkenyl groups (in particular $C_{4-6}$ cycloalkenyl groups), such as cyclopropenyl, cyclobutenyl, cyclopentenyl, cyclohexenyl and cyclooctenyl groups.

Among the cycloalkynyl groups, there may be mentioned, for example, $C_{3-10}$ cycloalkynyl groups, preferably $C_{4-8}$ cycloalkynyl groups (in particular $C_{4-6}$ cycloalkynyl groups), such as cyclopropynyl, cyclobutynyl, cyclopentynyl, cyclohexynyl and cyclooctynyl groups.

The above aliphatic hydrocarbon groups may be substituted. As the substituent or substituents, there may be mentioned halogen atoms such as fluorine, chlorine and bromine atoms; $C_{1-4}$ alkyl groups such as methyl and ethyl groups; acyl groups [$C_{1-4}$ alkylcarbonyl groups such as acetyl group; $C_{6-10}$ arylcarbonyl groups such as benzoyl group; etc.]; acyloxy groups [$C_{1-4}$ alkylcarbonyloxy groups such as acetyloxy group; $C_{6-10}$ arylcarbonyloxy groups such as benzoyloxy group; etc.]; alkoxy groups (e.g. $C_{1-4}$ alkoxy groups) such as methoxy and ethoxy groups; alkoxycarbonyl groups (e.g. $C_{1-4}$ alkoxycarbonyl groups) such as methoxycarbonyl group; and aryloxy groups such as phenoxy group, among others.

In a preferred embodiment, the chain or cyclic hydrocarbon group may be substituted by an aromatic group, for example a homocyclic group (aryl group) or a heterocyclic group (heteroaromatic group). Among such aromatic groups, the aryl group includes $C_{6-10}$ aryl groups such as phenyl and naphthyl groups and the heteroaromatic group includes 5- to 8-membered cyclic groups containing at least one hetero atom selected from among nitrogen, oxygen and sulfur atoms, for example pyridinyl, piperidyl and furfuryl groups. As the aliphatic hydrocarbon group substituted by an aromatic group, there may be mentioned arylalkyl groups (e.g. $C_{6-10}$ aryl-$C_{1-4}$ alkyl groups such as benzyl and phenethyl groups), arylalkenyl groups (e.g. $C_{6-10}$ aryl-$C_{2-4}$ alkenyl groups) and arylalkynyl groups (e.g. $C_{6-10}$ aryl-$C_{2-4}$ alkynyl groups), among others. These aromatic groups may be substituted by an appropriate substituent or substituents. As the appropriate substituents, there may be mentioned, halogen atoms, such as chlorine, bromine and fluorine atoms, alkyl groups (e.g. $C_{1-4}$ alkyl groups), ketone groups (e.g. $C_{1-6}$ alkylcarbonyl groups such as methylcarbonyl and ethylcarbonyl groups, $C_{6-10}$ arylcarbonyl groups such as phenylcarbonyl), alkoxy groups (e.g. $C_{1-6}$ alkoxy groups such as methoxy, ethoxy, propoxy and butoxy groups), aryloxy groups (e.g. phenoxy group) and ester groups (e.g. $C_{1-6}$ alkoxycarbonyl groups such as methoxycarbonyl and ethoxycarbonyl groups, aryloxycarbonyl groups such as phenoxycarbonyl group, etc.), among others.

$R^2$ and $R^3$ may bond together to form a ring (e.g. a $C_{3-6}$ cycloalkane ring or a 5- to 10-membered heterocycle).

Preferred as $R^1$ are straight or branched alkyl groups (e.g. $C_{1-6}$ alkyl groups such as methyl, ethyl, isopropyl and tert-butyl group), cycloalkyl groups (e.g. $C_{3-10}$ cycloalkyl groups, in particular $C_{5-8}$ cycloalkyl groups such as cyclohexyl group) and aralkyl groups (e.g. $C_{6-10}$ aryl-$C_{1-4}$ alkyl groups, in particular phenyl-$C_{1-4}$ alkyl groups such as benzyl and phenethyl groups). Preferred as $R^2$ and $R^3$ are a hydrogen atom and alkyl groups (e.g. $C_{1-4}$ alkyl groups, in particular $C_{1-2}$ alkyl groups such as methyl group).

As such cyclic esters (1), there may be mentioned, among others, 6-$C_{1-4}$ alkoxycarbonylmethyl-2,2-di$C_{1-4}$ alkyl-4H-1,3-dioxin-4-one (e.g. 6-methoxycarbonylmethyl- 2,2-dimethyl-4H-1,3-dioxin-4-one, 6-ethoxycarbonylmethyl-2,2-dimethyl-4H-1,3-dioxin-4-one, 6-isopropoxycarbonylmethyl-2,2-dimethyl-4H-1,3-dioxin-4-one and 6-tert-butoxycarbonylmethyl-2,2-dimethyl-4H-1,3-dioxin-4-one); 6-$C_{3-10}$ cycloalkyloxycarbonylmethyl-2,2-di$C_{1-4}$ alkyl-4H-1,3-dioxin-4-one (e.g. 6-cyclohexyloxycarbonylmethyl-2,2-dimethyl-4H-1,3-dioxin-4-one); and 6-$C_{6-10}$ aryl-$C_{1-4}$ alkyloxycarbonylmethyl-2,2-di$C_{1-4}$ alkyl-4H-1,3-dioxin-4-one (e.g. 6-benzyloxycarbonylmethyl-2,2-dimethyl-4H-1,3-dioxin-4-one).

[Process for Producing the Cyclic Esters]

The above cyclic esters (1) can be produced by reacting a halogen compound represented by the following formula (2) with carbon monoxide and an alcohol or water (in particular an alcohol) represented by the following formula (3).

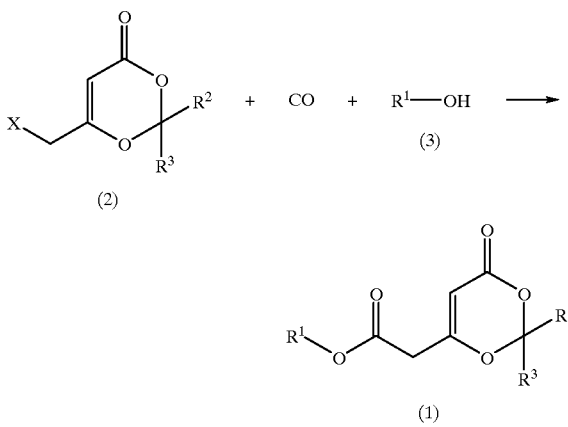

Referring to the above halogen compound (2), X is, for example, a halogen atom such as a fluorine, chlorine, bromine or iodine atom. Among these halogen atoms, a bromine or iodine atom (in particular an iodine atom) is preferred. The above halogen compound (2) is useful as an intermediate for the production of the above cyclic esters (1).

According to the alcohol species employed, the reaction may proceed faster when, among the compounds represented by the above formula (2), one in which X is a bromine or iodine atom (in particular iodine atom) is used than when other halogen compounds (e.g. 6-chloromethyl-4H-1,3-dioxin-4-one) are used.

The compound in which X is an iodine or bromine atom (6-iodomethyl-4H-1,3-dioxin-4-one or 6-bromomethyl-4H-1,3-dioxin-4-one) may be synthesized in advance or a raw material capable of forming a compound in which X is an iodine or bromine atom (6-iodomethyl-4H-1,3-dioxin-4-one or 6-bromomethyl-4H-1,3-dioxin-4-one) in the reaction system may be used. In cases where X is a fluorine or chlorine atom, the atom X may be converted to an iodine or bromine atom by adding an iodinating or brominating agent to the reaction system. The iodinating agent includes iodine, alkali metal iodides (lithium iodide, potassium iodide, sodium iodide, etc.) and so on and the brominating agent includes bromine, alkali metal bromides (lithium bromide, potassium bromide, sodium bromide, etc.) and so forth. Thus, 6-iodomethyl-4H-1,3-dioxin-4-one may be formed in the system by adding, for example 6-chloromethyl-4H-1,3-dioxin-4-one and an iodide, such as potassium iodide or sodium iodide, or iodine to the reaction system.

The iodinating or brominating agent may be used in an amount of 1 mole per 1 mole of the halogen compound in which X is a chlorine or fluorine atom or in a catalytic amount. Thus, usually, the iodinating or brominating agent is used in an amount of about 0.001 to 0.8 mole, preferably about 0.005 to 0.3 mole, more preferably about 0.01 to 0.2 mole, per 1 mole of the halogen compound.

The quantity ratio between the starting materials, namely the halogen compound (2) and the alcohol or water, is determined taking into consideration the extent of progress of the desired reaction, economical reasons and the mode of reaction as employed. Usually, the alcohol or water is used in an amount within the range of about 0.1 to 100,000 moles, preferably about 0.5 to 1,000 moles, more preferably about 0.8 to 100 moles, per 1 mole of the halogen compound (2). The reaction may also be carried out using the alcohol or water as a solvent.

Carbon monoxide is used in an amount of not less than 1 mole (for example about 1 to 10,000 moles, preferably about 1 to 1,000 moles, more preferably about 1 to 100 moles) per 1 mole of the halogen compound (2). The reaction is usually carried out in a carbon monoxide-containing atmosphere.

The reaction with carbon monoxide is preferably carried out in the presence of a carbonylation catalyst, for example a catalyst constituted of a platinum group metal.

As examples of the platinum group metal to be used as the catalyst, there may be mentioned platinum group metals described in J. Dealey: "Inorganic Chemistry", translated into Japanese by H. Hamaguchi and H. Kanno, published by Tokyo Kagaku Dojin (1982), page 360 or elsewhere, for example metals of group 8 of the Periodic Table (e.g. iron, ruthenium, osmium, etc.), group 9 metals (e.g. cobalt, rhodium, iridium, etc.), group 10 metals (e.g. nickel, palladium, platinum, etc.) and so forth. The catalyst may comprise these metals singly or a combination of two or more of them. Among these metals, group 10 metals (in particular palladium) are preferred.

The catalyst is only required to comprise a platinum group metal. Thus, such a metal as a simple substance may be used or a compound containing such a metal element may be used. As examples of the platinum group metal-containing compound, there may be mentioned metal salts, for example inorganic acid salts [e.g. hydrochloric acid salts, sulfuric acid salts, nitric acid salts, salts with carbonic acid (e.g. carbonates, hydrogen carbonates), salts with phosphoric acid (e.g. phosphates, hydrogen phosphates, dihydrogen phosphates), boric acid salts], organic acid salts (e.g. carboxylic acid salts such as formates, acetates, lactates, oxalates), halides (e.g. chlorides, bromides) and complexes resulting from coordination of a ligand with these metal components or salts thereof (e.g. tetrakistriphenylphosphinepalladium(0)), among others. As examples of the ligand, there may be mentioned phosphorus compounds such as phosphines (e.g. trialkylphosphines such as tributylphosphine, tricycloalkylphosphines such as tricyclohexylphosphine, triarylphosphines such as triphenylphosphine), nitrile, OH (hydroxo), alkoxy groups (e.g. methoxy and ethoxy groups), acyl groups (e.g. acetyl and propionyl groups), alkoxycarbonyl groups (e.g. methoxycarbonyl and ethoxycarbonyl groups), acetylacetonato, cyclopentadienyl group, halogen atoms, CO, $H_2O$ (aquo), nitrogen-containing compounds (e.g. $NH_3$, $NO_2$, $NO_3$, alkylenediamines, pyridine) and so forth.

The valence of the metal of the catalyst (platinum group metal component) is not particularly restricted but usually is 0 to 4, preferably about 0 to 2. The catalyst mentioned above may be a homogeneous one or a heterogeneous one. The catalyst component may be used as a solid catalyst supported on an appropriate support (e.g. a porous support such as activated carbon, silica (silica gel), alumina, zeolite, bentonite). These catalysts may be used alone or two or more of them may be used combinedly.

When the catalyst is a palladium-based one, for instance, the catalyst includes, among others, palladium nitrate, palladium chloride, palladium acetate, acetylacetonatopalladium(II), tetraamminepalladium(II) chloride, bis(ethylenediamine)palladium(II) chloride, potassium tetrachloropalladate(II), potassium tetranitropalladate (II), dichlorobis(trialkylphosphine)palladium(II), dimethylbis(triethylphosphine)palladium(II), biscyclopentadienylpalladium(II), tricarbonylcyclopentadienylpalladium(I), dichloro-$\mu$-bis[bis(dimethylphosphino)methane]dipalladium(I), tetrakis(triphenylphosphine)palladium(0), bis(tricyclohexylphosphine)palladium(0), tetrakis(triethylphosphito)palladium(0), carbonyltris(triphenylphosphine)palladium(0), bis(cycloocta-1,5-diene)palladium(0) and tris(dibenzylideneacetone)dipalladium(0).

Although the amount of the catalyst is not particularly restricted, the catalyst is used usually in an amount of 0.001 to 1 mole, preferably 0.003 to 0.5 mole, more preferably 0.005 to 0.5 mole (e.g. 0.01 to 0.2 mole), per 1 mole of the halogen compound (2).

As the reaction progresses, a hydrohalic acid is generated in the reaction system. For neutralizing this hydrohalic acid, a base may be added to the reaction system. As examples of the base, there may be mentioned inorganic bases, for example alkali metal hydroxides (e.g. sodium hydroxide, potassium hydroxide), alkali metal carbonates (e.g. sodium carbonate, potassium carbonate), alkali metal hydrogen carbonates (e.g. sodium hydrogen carbonate, potassium hydrogen carbonate), alkaline earth metal hydroxides (e.g. calcium hydroxide, magnesium hydroxide), alkaline earth metal carbonates (e.g. magnesium carbonate, calcium carbonate), alkaline earth metal hydrogen carbonates (e.g. magnesium hydrogen carbonate, calcium hydrogen carbonate) and the like; organic bases or amines, for example alkylamines (e.g. tertiary amines, for example tri-$C_{1-4}$ alkylamines such as triethylamine), heterocyclic amines (e.g. pyridine), $C_{1-4}$ alkylanilines (e.g. tertiary amines such as N,N-dimethylaniline); alkali metal carboxylates (e.g. sodium acetate, potassium acetate), alkaline earth metal carboxylates (e.g. magnesium acetate, calcium acetate) and so forth. These bases may be used singly or two or more of them may be used in combination. It seems that the use of an organic base or amine (e.g. tertiary amine) lead to an improved selectivity.

In carrying out the reaction, a solvent may be used. When a solvent is used, the solvent may be any one, without any particular limitation, provided that the progress of the reaction is not inhibited thereby but the reactants are soluble therein. As examples of the solvent, there may be mentioned ketones such as acetone and methyl ethyl ketone; ethers such as tetrahydrofuran and dioxane; nitriles such as acetonitrile; sulfoxides such as dimethylsulfoxide; sulfones such as sulfolane; aliphatic hydrocarbons such as pentane and hexane; aromatic hydrocarbons such as benzene and toluene; halogen-containing compounds such as methylene chloride, chloroform, bromoform, chlorobenzene and bromobenzene. When an alcohol (e.g. methanol, ethanol, tert-butanol) is used as the solvent, the starting material alcohol itself is preferably used as the solvent. These solvents may be used singly or two or more of them may be used in combination. The amount of the solvent is not particularly restricted but should be such that the reactants (halogen compound etc.) can be dissolved therein sufficiently.

This reaction is carried out usually at about ordinary pressure (or atmospheric pressure) to 500 atmospheres (about 50 MPa), preferably at about ordinary pressure to 100 atmospheres (about 10 MPa), more preferably at about ordinary pressure to 50 atmospheres (about 5 MPa) (e.g. about ordinary pressure to 10 atmospheres (about 1 MPa)). For apparatus and/or operational reasons, for instance, the reaction may be carried out under reduced pressure. The selectivity seems to be improved when the reaction is carried out under pressure (e.g. about 2 to 50 atmospheres (about 0.2 to 5 MPa), preferably about 5 to 30 atmospheres (about 0.5 to 3 MPa)).

The carbon monoxide may be pure carbon monoxide gas or may be used as a mixed gas with an inert gas (e.g. nitrogen, argon, helium). Thus, the gaseous phase may contain an inert gas, such as nitrogen, argon or helium, in addition to carbon monoxide. The method of causing the gaseous component to dissolve in the liquid phase is not particularly restricted. For effecting the reaction, it is only necessary for carbon monoxide to come into contact with the other reactants. If it is soluble to a satisfactory extent, it may be dissolved by gas-liquid contacting or a carbon monoxide-containing gas may be blown into the liquid phase through a blowing tube, for instance.

The reaction temperature is not particularly restricted, either. Thus, the reaction temperature may be between the melting point to the boiling point of the reaction system under such reaction conditions as mentioned above. Usually, it is −30° C. to 200° C., preferably about −10° C. to 100° C. This reaction may be carried out batchwise, semi-batchwise or continuously.

Among the cyclic esters mentioned above, those compounds in which $R^1$ is a hydrogen atom (carboxylic acids) may also be produced by carrying out the reaction using an alcohol and then subjecting the products to conventional ester hydrolysis to thereby eliminate the alcohol-derived alkyl group by hydrolysis.

After completion of the reaction, the product can readily be separated and purified by conventional separation/purification means, for example filtration, concentration, distillation, extraction, crystallization, recrystallization, adsorption or column chromatography, or a combination of these means.

[Process for Producing the Dicarboxylic Acid Esters]

The dicarboxylic acid esters (3-oxopentanedicarboxylic acid esters) represented by the following formula (5) can be produced by reacting the above cyclic esters (1) with an alcohol or water (in particular alcohol) represented by the following formula (4).

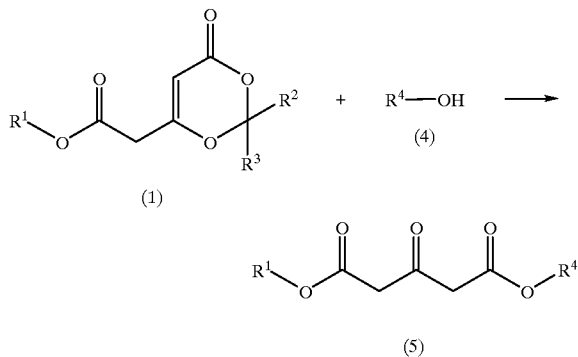

In the above formula, $R^1$, $R^2$, $R^3$ and $R^4$ are the same or different and each represents a hydrogen atom or a straight or branched aliphatic hydrocarbon group or saturated or unsaturated cyclic aliphatic hydrocarbon group, which may optionally be further substituted by an aromatic group.

As specific examples of the chain aliphatic hydrocarbon group and cyclic aliphatic hydrocarbon group represented by $R^1$, $R^2$, $R^3$ and $R^4$ and of the aromatic group which these aliphatic hydrocarbon groups may have, there may be mentioned, among others, those species mentioned hereinabove referring to $R^1$ to $R^3$. Preferred as $R^4$ are a hydrogen atom, $C_{1-10}$ aliphatic hydrocarbon groups ($C_{1-6}$ alkyl groups such as methyl, ethyl group, in particular $C_{1-4}$ alkyl groups) and $C_{4-8}$ alicyclic hydrocarbon groups, among others.

In this process, the cyclic esters may be prepared not only by the above-mentioned process for producing cyclic esters according to the present invention but also by other processes.

The quantity ratio between the starting materials, namely cyclic ester and alcohol or water, is determined considering the extent of progress of the desired reaction, economic reasons and the reaction mode employed. Usually, the alcohol or water is used in an amount of 0.1 to 100,000 moles, preferably 0.5 to 1,000 moles, more preferably about 0.8 to 100 moles, per 1 mole of the cyclic ester. In carrying out the reaction, the alcohol or water may be used also as a solvent.

Mere heating of the reaction system can cause this reaction to proceed. However, for promoting the progress of the reaction, a catalyst may be used. As examples of the catalyst, there may be mentioned inorganic acids (e.g. sulfuric acid, hydrochloric acid, phosphoric acid, nitric acid), organic acids (sulfonic acids, for example $C_{1-6}$ alkanesulfonic acids such as methanesulfonic acid and ethanesulfonic acid, aromatic sulfonic acids such as paratoluenesulfonic acid and benzenesulfonic acid, and the like; organic carboxylic acids, for example $C_{1-10}$ saturated or unsaturated mono- or polycarboxylic acids such as acetic acid and propionic acid; halogenated organic acids, for example halogenated carboxylic acids such as trichloroacetic acid and trifluoroacetic acid; halogenated alkanesulfonic acids such as trifluoromethanesulfonic acid and the like) and solid acids [sulfuric acid salts (e.g. calcium sulfate), metal oxides (e.g. $SiO_2$, $Al_2O_3$), zeolites (e.g. acidic OH-containing Y, X or A type zeolites), heteropolyacids, ion exchange resins (e.g. H type cation exchange resins)], among others. The catalyst may be used singly or in combination.

The amount of the catalyst is not particularly restricted but, usually is 0.001 to 1 mole, preferably 0.005 to 0.5 mole, more preferably about 0.01 to 0.2 mole, per 1 mole of the cyclic ester.

In carrying out the reaction, a solvent may be used. When a solvent is used, the solvent may be any one, without any particular limitation, provided that the progress of the reaction is not inhibited thereby but the reactants are soluble therein. For example, any of those solvents which can be used in the production of the cyclic esters mentioned above can be used as the solvent.

This reaction is carried out usually at ordinary or atmospheric pressure. For apparatus and/or operational reasons, for instance, the reaction may be carried out under reduced pressure or under pressure.

The reaction temperature may be between the melting point to the boiling point of the reaction system under such reaction conditions as mentioned above. Usually, it is −30° C. to 300° C., preferably about −10° C. to 200° C. This reaction may be carried out batchwise, semi-batchwise or continuously.

Among the above-mentioned dicarboxylic acid esters of the above formula (5), those derivatives in which $R^1$ and/or $R^4$ is a hydrogen atom may also be produced by carrying out the reaction using an alcohol and then subjecting the products to conventional ester hydrolysis to thereby eliminate the alcohol-derived alkyl group by hydrolysis.

The products can be isolated in the same manner as mentioned above relative to the production of the cyclic esters.

When the production of such a cyclic ester as mentioned above is followed by the production of such a dicarboxylic acid ester as mentioned above, the cyclic ester obtained by the former reaction may be isolated and then subjected to the latter reaction or the cyclic ester formed in the reaction system may be subjected, as it is, to the latter reaction, without separation/purification.

According to the present invention, 3-oxopentanedicarboxylic acid esters or raw materials therefor, namely 6-alkoxycarbonylmethyl-4H-1,3-dioxin-4-ones, which are novel compounds, can be synthesized efficiently under mild or moderate reaction conditions using only compounds relatively easy to obtain and handle. Further, not only symmetrical ones but also 3-oxopentanedicarboxylic acid esters having an unsymmetrical structure can be synthesized with ease.

EXAMPLES

The following examples illustrate the present invention in more detail. They are, however, by no means limitative of the scope of the invention. In the following examples, a methyl group is sometimes abbreviated as Me, an ethyl group as Et, an isopropyl group as i-Pr, a tertiary butyl group as t-Bu, a benzyl group as $PhCH_2$, a cyclohexyl group as c-Hex, trimethylsilane as TMS and tetrahydrofuran as THF.

The IR spectra were recorded on a Perkin-Elmer 1600 Series FT-IR spectrophotometer.

The NMR spectra were recorded on a Bruker AM500 spectrometer at 500 MHz ($^1$H-NMR) or 125.7 MHz ($^{13}$C-NMR) with TMS as an internal standard.

The MS spectra were recorded on a Thermoquest LCQ spectrometer using the syringe method and the ionization mode APCI for detecting positive ions.

Example 1

Synthesis of 6-iodomethyl-2,2-dimethyl-4H-1,3-dioxin-4-one

Sodium iodide (2.16 g) was dissolved in 16 mL of acetone, 2.00 g of 2,2-dimethyl-6-chloromethyl-1,3-dioxin- 4-one diluted with 4 mL of acetone was added, and the mixture was stirred at room temperature for 2 hours. The insoluble matter was removed from the reaction mixture by filtration and the filtrate was concentrated. The residue was dissolved in 20 mL of chloroform, the insoluble matter was again filtered off and the filtrate was concentrated. The thus-obtained residue was purified by silica gel column chromatography (solvent: hexane/ethyl acetate=1/1 (volume ratio)) to give 2.65 g of 6-iodomethyl-2,2-dimethyl-4H-1,3-dioxin-4-one as a yellow liquid. The NMR spectrum of this compound is shown below.

$^1$H-NMR (CD$_3$Cl) ppm: 1.71 (s, 6H, Me), 3.83 (s, 2H, CH$_2$I), 5.52 (s, 1H, =CH).

Example 2

Synthesis of 6-methoxycarbonylmethyl-2,2-dimethyl-4H-1,3-dioxin-4-one (synthesis from 6-iodomethyl-2,2-dimethyl-4H-1,3-dioxin-4-one)

A 50-mL two-necked flask was charged with 0.100 g (0.564 mmol) of palladium chloride, 0.782 g (5.66 mmol) of potassium carbonate and 0.940 g (5.66 mmol) of potassium iodide, and a carbon monoxide atmosphere was produced in the system by introducing carbon monoxide using a balloon (atmospheric pressure). To this system were added 10 mL of methanol and 1.0 g (5.66 mmol) of 6-chloromethyl-2,2-dimethyl-4H-1,3-dioxin-4-one, and the mixture was stirred at room temperature for 18 hours.

After completion of the reaction, the reaction mixture was filtered and the filtrate obtained was concentrated. To this residue were added 25 mL of ethyl acetate and 25 mL of water and, after mixing up, the mixture was allowed to separate into two layers. The upper layer (organic layer) was dried over anhydrous sodium sulfate, filtered and concentrated to give 0.408 g of a dark brown residue.

This residue was subjected to $^1$H-NMR spectroscopy for identification, and 6-methoxycarbonylmethyl-2,2-dimethyl-4H-1,3-dioxin-4-one and 2,2,6-trimethyl-4 H-1,3-dioxin-4-one were detected in a molar ratio of the former/the latter= 1.0:1.3. No remnant of the starting material 6-chloromethyl-2,2-dimethyl-4H-1,3-dioxin-4-one was detected and other products were nearly absent.

This mixture was purified by silica gel thin layer chromatography (mobile phase: hexane/ethyl acetate=2/1 (volume ratio)) and 68.1 mg of the desired product 6-methoxycarbonylmethyl-2,2-dimethyl-4H-1,3-dioxin-4-one. The Rf value was 0.25. The IR spectrum, NMR spectrum and MS spectrum of this compound are shown below.

IR (neat): 3000, 2956, 1732, 1643 cm$^{-1}$ $^1$H-NMR (CD$_3$Cl) ppm: 1.71 (s, 6H, CMe$_2$), 3.29 (s, 2H, CH$_2$CO), 3.75 (s, 3H, COOMe), 5.40 (s, 1H, CH=C)

$^{13}$C-NMR (CDCl$_3$) ppm: 24.9 (CMe$_2$), 39.2 (CH$_2$CO), 52.5 (OMe), 96.5 (HC=), 107.3 (Me$_2$C), 160.7 (O=CCH$_2$C=), 163.7 (COOMe), 167.6 (=C—CO—O—CMe$_2$—)

CI-MS (m/z): 201 (M$^+$+1, 100%), 143 (M$^+$+1-58).

Example 3

Synthesis of 6-methoxycarbonylmethyl-2,2-dimethyl-4H-1,3-dioxin-4-one (synthesis from 6-chloromethyl-2,2-dimethyl-4H-1,3-dioxin-4-one)

The reaction was carried out in the same manner as in Example 2 except that potassium iodide was not used. The reaction mixture was then treated in the same manner as mentioned above to give 0.500 g of a residue. This residue was subjected to $^1$H-NMR spectrometry for identification, and 6-methoxycarbonylmethyl-2,2 -dimethyl-4H-1,3-dioxin-4-one and 2,2,6-trimethyl-4H-1,3-dioxin-4-one could be detected in a molar ratio of the former/the latter= 1.0:3.0.

Example 4

Synthesis of 6-methoxycarbonylmethyl-2,2-dimethyl-4H-1,3-dioxin-4-one (change of palladium catalyst species)

The reaction was carried out in the same manner as in Example 2 except that 0.130 g (0.579 mmol) of palladium acetate was used as the catalyst in lieu of palladium chloride and that potassium iodide was not used. The reaction mixture was treated in the same manner as mentioned above to give 0.428 g of a residue. This residue was subjected to $^1$H-NMR spectroscopy for identification, and 6-methoxycarbonylmethyl-2,2-dimethyl-4H-1,3-dioxin-4-one and 2,2,6-trimethyl-4H-1,3-dioxin-4-one could be detected in a molar ratio of the former/the latter=1.0:9.0.

Example 5

Synthesis of 6-isopropoxycarbonylmethyl-2,2-dimethyl-4H-1,3-dioxin-4-one

The reaction was carried out in the same manner as in Example 2 except that 10 mL of isopropyl alcohol was used as the alcohol in lieu of methanol. The reaction mixture was treated in the same manner as mentioned above and the organic layer obtained by phase separation was dried and concentrated to give 0.999 g of nearly pure 6-isopropoxycarbonylmethyl-2,2-dimethyl-4H-1,3-dioxin-4-one. The yield of 6-isopropoxycarbonylmethyl-2,2 -dimethyl-4H-1,3-dioxin-4-one was 74 mol % based on the starting material 6-chloromethyl-2,2-dimethyl-4H-1,3-dioxin-4-one. The NMR spectrum data on this compound are shown below.

$^1$H-NMR (CD$_3$Cl) ppm: 1.26 (d, J=6.4 Hz, 6H, CHMe$_2$), 1.71 (s, 6H, CMe$_2$), 3.23 (s, 2H, CH$_2$CO), 5.0–5.1 (m, 1H, CHMe$_2$), 5.38 (s, 1H, CH=C).

Another product was 2,2,6-trimethyl-4H-1,3-dioxin-4-one and this was formed in 5.8 mol % yield based on the starting material 6-chloromethyl-2,2-dimethyl-4H-1,3-dioxin-4-one. No remnant of the starting material 6-chloromethyl-2,2-dimethyl-4H-1,3-dioxin-4-one could be detected.

Example 6

Synthesis of 6-tert-butoxycarbonylmethyl-2,2-dimethyl-4H-1,3-dioxin-4-one

The reaction was carried out in the same manner as in Example 2 except that 10 mL of tert-butyl alcohol was used as the alcohol in lieu of methanol. The reaction mixture was treated in the same manner as mentioned above and the organic layer obtained by phase separation was dried and concentrated to give 0.44 g of 6-tert-butoxycarbonylmethyl-2,2-dimethyl-4H-1,3-dioxin-4-one. The NMR spectrum data on this compound are shown below.

$^1$H-NMR (CD$_3$Cl) ppm: 1.46 (s, 9H, t-Bu), 1.71 (s, 6H, CMe$_2$), 3.17 (s, 2H, CH$_2$CO), 5.36 (s, 1H, CH=C).

Another product was 2,2,6-trimethyl-4H,1,3 -dioxin-4-one. No remnant of the starting material 6-chloromethyl-2, 2-dimethyl-4H-1,3-dioxin-4-one could be detected.

Example 7

Synthesis of 6-ethoxycarbonylmethyl-2,2-dimethyl-4H-1,3-dioxin-4-one

The reaction was carried out in the same manner as in Example 2 except that 10 mL of ethanol was used as the alcohol in lieu of methanol. The reaction mixture was treated in the same manner as mentioned above and the organic layer obtained by phase separation was dried and concentrated to give 0.70 g of 6-ethoxycarbonylmethyl-2,2-dimethyl-4H-1,3-dioxin-4-one. The NMR spectrum data on this compound are shown below.

$^1$H-NMR (CD$_3$Cl) ppm: 1.28 (t, J=7.1 Hz, 3H, CH$_3$CH$_2$), 1.71 (s, 6H, CMe$_2$), 3.25 (s, 2H, CH$_2$CO), 4.20 (q, J=7.1 Hz, 2H, CH$_3$CH$_2$), 5.39 (s, 1H, CH=C).

Another product was 2,2,6-trimethyl-4H-1,3-dioxin-4-one. No remnant of the starting material 6-chloromethyl-2,2-dimethyl-4H-1,3-dioxin-4-one could be detected.

Example 8

Synthesis of 6-benzyloxycarbonylmethyl-2,2-dimethyl-4H-1,3-dioxin-4-one

The reaction was carried out in the same manner as in Example 2 except that 0.6 g of benzyl alcohol was used as the alcohol in lieu of methanol and that 10 mL of THF was used as a solvent. The reaction mixture was treated in the same manner as mentioned above and the organic layer obtained by phase separation was dried and concentrated to give 0.75 g of 6-benzyloxycarbonylmethyl-2,2-dimethyl-4H-1,3-dioxin-4-one. The NMR spectrum data on this compound are shown below. No remnant of the starting material 6-chloromethyl-2,2-dimethyl-4H-1,3-dioxin-4-one could be detected.

$^1$H-NMR (CD$_3$Cl) ppm: 1.63 (s, 6H, CMe$_2$), 3.30 (s, 2H, CH$_2$CO), 5.16 (s, 2H, PhCH$_2$), 5.38 (s, 1H, CH=C), 7.3–7.5 (m, 5H, Ph).

Example 9

Synthesis of 6-cyclohexyloxycarbonylmethyl-2,2-dimethyl-4H-1,3-dioxin-4-one

The reaction was carried out in the same manner as in Example 2 except that 0.6 g of cyclohexanol was used as the alcohol in lieu of methanol and that 10 mL of acetonitrile was used as a solvent. The reaction mixture was treated in the same manner as mentioned above and the organic layer obtained by phase separation was dried and concentrated to give 0.92 g of 6-cyclohexyloxycarbonylmethyl-2,2-dimethyl-4H-1,3-dioxin-4-one. The NMR spectrum data on this compound are shown below. No remnant of the starting material 6-chloromethyl-2,2-dimethyl-4H-1,3-dioxin-4-one could be detected.

$^1$H-NMR (CD$_3$Cl) ppm: 1.1–2.0 (m, 10H, methylenes of cyclohexane ring), 1.71 (s, 6H, CMe$_2$), 3.24 (s, 2H, CH$_2$CO), 4.8–4.9 (m, 1H, OCH(CH$_2$)$_2$), 5.38 (s, 1H, CH=C).

The results obtained in Examples 2 to 9 are summarized in Table 1.

TABLE 1

| | | | ($R^2$=$R^3$=Me) | | | |
|---|---|---|---|---|---|---|
| | | | | Yield (mole %) | Conversion of | Selectivity for |
| Example | $R^1$ | Catalyst | Additive | Desired product | By-product | starting material (mol %) | desired product (mol %) |
| 2 | Me | PdCl$_2$ | KI | 19 | 24 | 43 | 44 |
| 3 | Me | PdCl$_2$ | — | 14 | 42 | 56 | 25 |
| 4 | Me | Pd(OAc)$_2$ | — | 5 | 46 | 51 | 10 |
| 5 | i-Pr | PdCl$_2$ | KI | 74 | 6 | 80 | 93 |
| 6 | t-Bu | PdCl$_2$ | KI | 34 | 22 | 56 | 61 |
| 7 | Et | PdCl$_2$ | KI | 58 | 6 | 64 | 90 |
| 8 | PhCH$_2$ | PdCl$_2$ | KI | 48 | 16 | 64 | 75 |
| 9 | c-Hex | PdCl$_2$ | KI | 61 | 14 | 75 | 81 |

In Table 1, the desired product is the 6-alkoxycarbonylmethyl-2,2-dimethyl-4H-1,3-dioxin-4-one and the by-product is 2,2,6-trimethyl-4H-1,3-dioxin-4-one.

Example 10

Synthesis of tert-butyl methyl 3-oxopentanedicarboxylate

6-Methoxycarbonylmethyl-2,2-dimethyl-4H-1,3-dioxin-4-one (51.7 mg, 0.258 mmol) and 20.6 mg (0.277 mmol) of tert-butyl alcohol were dissolved in 12 mL of chloroform and the solution was sealed in a tube. This system was heated at 80° C. for 9 hours and the desired product tert-butyl methyl 3-oxopentanedicarboxylate was obtained in 81 mol % yield. The NMR spectrum data on this compound are shown below. No by-product was present and the starting material 6-ethoxycarbonylmethyl-2,2-dimethyl-4H-1,3-dioxin-4-one was recovered.

$^1$H-NMR (CD$_3$Cl) ppm: 1.47 (s, 9H, t-Bu), 3.51 (s, 2H, CH$_2$), 3.61 (s, 2H, CH$_2$), 3.74 (s, 3H, Me).

Example 11

Synthesis of 6-methoxycarbonylmethyl-2,2-dimethyl-4H-1,3-dioxin-4-one under pressurization with carbon monoxide The reaction was carried out in the same manner as in Example 2 except that 0.094 g (0.566 mmol) of potassium iodide was used and that the reaction system was maintained in a carbon monoxide atmosphere at 1 MPa using a 100-mL microcylinder.

After completion of the reaction, the reaction mixture was treated in the same manner as mentioned above and the product was subjected to $^1$H-NMR for identification. 6-Methoxycarbonylmethyl-2,2-dimethyl-4H-1,3-dioxin-4-one and 2,2,6-trimethyl-4H-1,3-dioxin-4-one could be detected in a molar ratio of the former/the latter=1.0:0.52. No remnant of the starting material 6-chloromethyl-2,2-dimethyl-4H-1,3-dioxin-4-one could be detected and almost no other products were present. In spite of the reduction in amount of potassium iodide, the reaction efficiently progressed and the selectivity was improved by carrying out the reaction under pressure (1 MPa).

Example 12

Synthesis of 6-methoxycarbonylmethyl-2,2-dimethyl-4H-1,3-dioxin-4-one under pressurization with carbon monoxide (using an amine)

The reaction was carried out in the same manner as in Example 11 except that 1.2 g (11.8 mmol) of triethylamine was used as the base in lieu of potassium carbonate.

After completion of the reaction, the reaction mixture was treated in the same manner as mentioned above and the product was subjected to $^1$H-NMR for identification. 6-Methoxycarbonylmethyl-2,2-dimethyl-4H-1,3-dioxin-4-one and 2,2,6-trimethyl-4H-1,3-dioxin-4-one could be detected in a molar ratio of the former/the latter=1.0:0.30. No remnant of the starting material 6-chloromethyl-2,2-dimethyl-4H-1,3-dioxin-4-one could be detected and almost no other products were present. The use of an organic base or amine as the base resulted in an improvement in selectivity.

Example 13

Synthesis of 6-methoxycarbonylmethyl-2,2-dimethyl-4H-1,3-dioxin-4-one (reduction in amount of Pd)

Palladium chloride (0.032 g, 0.18 mmol), 6.0 g (59.2 mmol) of triethylamine, 0.470 g (2.83 mmol) of potassium iodide, 25 mL of methanol and 5.0 g (28.3 mmol) of 6-chloromethyl-2,2-dimethyl-4H-1,3-dioxin-4-one were placed in a 100-mL microcylinder, and the mixture was stirred at room temperature for 22 hours.

After completion of the reaction, the reaction mixture was filtered and the filtrate was concentrated. To this residue was added 30 mL of ethyl acetate and the mixture was washed with two 30-mL portions of water. The organic layer was dried over anhydrous sodium sulfate, filtered and concentrated to give 4.013 g of a dark brown residue.

This reaction mixture was subjected to $^1$H-NMR spectroscopy for identification. 6-Methoxycarbonylmethyl-2,2-dimethyl-4H-1,3-dioxin-4-one and 2,2,6-trimethyl-4H-1,3-dioxin-4-one could be detected in a molar ratio of the former/the latter=1.0:0.27. No remnant of the starting material 6-chloromethyl-2,2 -dimethyl-4H-1,3-dioxin-4-one could be detected and almost no other products were present.

Example 14

Synthesis of 6-methoxycarbonylmethyl-2,2-dimethyl-4H-1,3-dioxin-4-one (reduction in amount of Pd)

The reaction was carried out in the same manner as in Example 13 except that 0.016 g (0.09 mmol) of palladium chloride was used and the mixture stirred at room temperature for 50 hours.

After completion of the reaction, the reaction mixture was subjected to H-NMR spectroscopy for identification. 6-Methoxycarbonylmethyl-2,2-dimethyl-4H-1,3-dioxin-4-one and 2,2,6-trimethyl-4H-1,3-dioxin-4-one could be detected in a molar ratio of the former/the latter=1.0:0.29. No remnant of the starting material 6-chloromethyl-2,2-dimethyl-4H-1,3-dioxin-4-one could be detected and almost no other products were present.

What is claimed is:

1. A process for producing dicarboxylic acid esters represented by the formula (5):

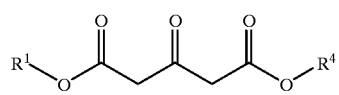

(5)

wherein $R^1$ and $R^4$ are the same or different and each represents a hydrogen atom or a chain or cyclic aliphatic hydrocarbon group, which is unsubstituted or is substituted by halogen atoms, $C_{1-4}$-alkyl groups, acyl groups, $C_{6-10}$-arylcarbonyl groups, acyloxy groups, $C_{6-10}$-arylcarbonyloxy groups, alkoxy, groups, alkoxycarbonyl groups, and aryloxy groups, or by an aromatic group, which comprises reacting a cyclic ester represented by the formula (1):

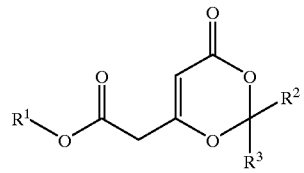

(1)

wherein, $R^1$, $R^2$, and $R^3$ are the same or different, $R^1$ is as defined above and $R^2$ and $R^3$ each represents a hydrogen atom or a chain or cyclic aliphatic hydrocarbon group, which is unsubstituted or is substituted by halogen atoms, $C_{1-4}$-alkyl groups, acyl groups, $C_{6-10}$-arylcarbonyl groups, acyloxy groups, $C_{6-10}$-arylcarbonyloxy groups, alkoxy groups, alkoxycarbonyl groups, and aryloxy groups, or by an aromatic group or $R^2$ and $R^3$ may bond together to form a ring, with an alcohol or water represented by the formula (4):

$$R^4\text{—OH} \tag{4}$$

wherein $R^4$ is as defined above.

2. The process of claim 1, wehrein $R^1$ and $R^4$ are the same or different and each represents a straight or branched alkyl group, a cycloalkyl group, or an aralkyl group.

3. The process of claim 1, wehrein $R^1$ and $R^4$ are the same or different and each represents a $C_{1-6}$-alkyl group, a $C_{3-10}$-cycloalkyl group, or a $C_{6-10}$-aryl-$C_{1-4}$-alkyl group.

* * * * *